US006168562B1

(12) United States Patent
Miller et al.

(10) Patent No.: US 6,168,562 B1
(45) Date of Patent: Jan. 2, 2001

(54) METHOD AND APPARATUS FOR DYNAMICALLY TAILORING BIOCHEMICAL BASED THERAPY PROGRAMS IN HUMAN

(75) Inventors: Steven L. Miller, Pacifica; Michael M. Merzenich, San Francisco; Bret E. Peterson, Lafayette, all of CA (US)

(73) Assignee: Scientific Learning Corporation, Berkeley, CA (US)

( * ) Notice: Under 35 U.S.C. 154(b), the term of this patent shall be extended for 0 days.

(21) Appl. No.: 09/100,663

(22) Filed: Jun. 18, 1998

Related U.S. Application Data

(63) Continuation of application No. 09/052,838, filed on Mar. 31, 1998.

(51) Int. Cl.[7] .................................................. A61N 5/00
(52) U.S. Cl. .............................................................. 600/300
(58) Field of Search .................................... 600/587, 595, 600/300, 301, 920

(56) References Cited

U.S. PATENT DOCUMENTS

| 5,678,571 | 10/1997 | Brown .................................. | 128/898 |
| 5,722,418 | 3/1998 | Bro ...................................... | 128/732 |
| 5,725,472 | 3/1998 | Weathers ............................... | 600/21 |
| 5,908,383 | * 6/1999 | Brynjestad ............................ | 600/300 |
| 5,910,107 | 6/1999 | Iliff ...................................... | 600/300 |
| 5,913,310 | 6/1999 | Brown .................................. | 128/897 |
| 5,954,641 | * 9/1999 | Kehr et al. ............................ | 600/300 |

FOREIGN PATENT DOCUMENTS

| WO 93/02622 | 2/1993 | (WO) | ............................. | A61B/5/16 |
| WO 94/04072 | 3/1994 | (WO) | ............................. | A61B/5/00 |
| WO 94/06088 | 3/1994 | (WO) | ............................. | G06F/15/42 |
| WO 95/29447 | 2/1995 | (WO) | ............................. | G06F/15/02 |
| WO 97/06730 | 2/1997 | (WO) | ......................... | A61B/5/0484 |
| WO 97/34526 | 9/1997 | (WO) | ............................. | A61B/5/05 |

OTHER PUBLICATIONS

Roger Jelliffe, et al., Adaptive control of drug dosage regimens: basic foundations, relevant issues, and clinical examples, International Journal of Bio–Medical Computing 36, (pp. 1–23), ©1994.

Schneider et al. Self–Regulation of Slow Cortical Potentials in Psychiatric Patients: Schizophrenia ©Dec. 1992, Biofeedback and Self–Regulation, vol. 17, No. 4, pp. 277–292.

Tretter F., Perspectives of Computer–Aided Therapy and Rehabilitation in Psychiatry, Jul. 1996, pp. 475–486.

Hermanutz M. and Gestrich J., Computer–assisted Attention Training in Schizophrenics, 1991, European Archives of Psychiatry and Clinical Neuroscience, vol. 240, pp. 282–287.

\* cited by examiner

*Primary Examiner*—Max Hindenburg
(74) *Attorney, Agent, or Firm*—Beyer Weaver & Thomas, LLP

(57) ABSTRACT

The invention relates, in one embodiment to a computer-implemented method for dynamically tailoring dosages of a biochemical compound administered to a human under a biochemical-based therapy program. The method includes administering a first plurality of stimulus exercises to the human over a period of time. The first plurality of stimulus exercises are administered to the human after at least one administration of the biochemical compound. The method also includes measuring responses from the first plurality of stimulus exercises to assess efficacy levels of the biochemical portion on the human as a function of time over the period of time. The method further includes dynamically modulating the dosages of the biochemical compound responsive to the efficacy levels measured from the first plurality of stimulus exercises. The modulating results in a first dosage configured to be administered to the human at a first administration time and a second dosage different from the first dosage configured to be administered to the human at a second administration time different from the first administration time.

19 Claims, 5 Drawing Sheets

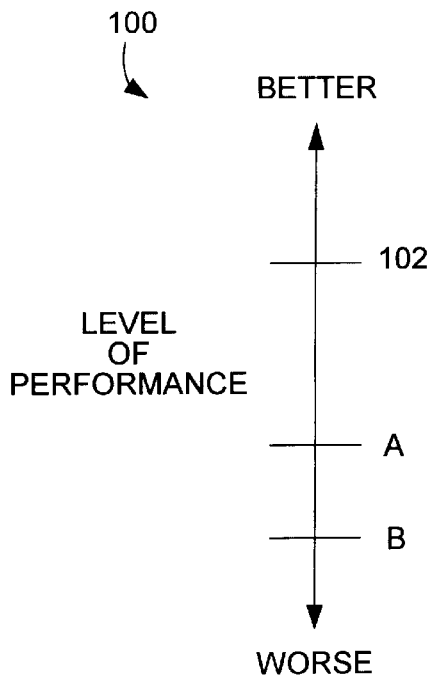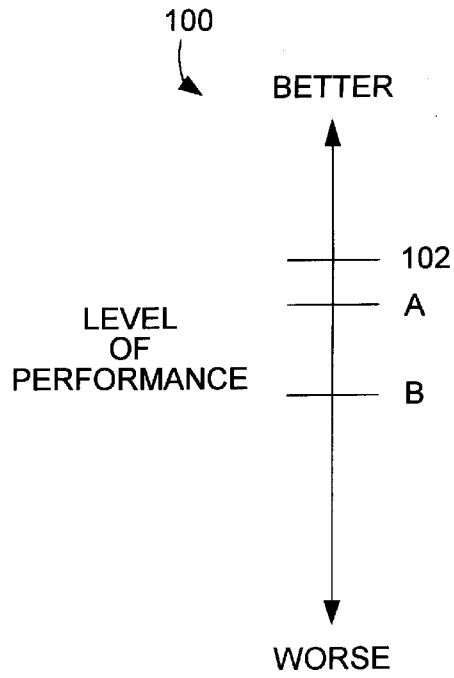
FIG. 1  FIG. 3
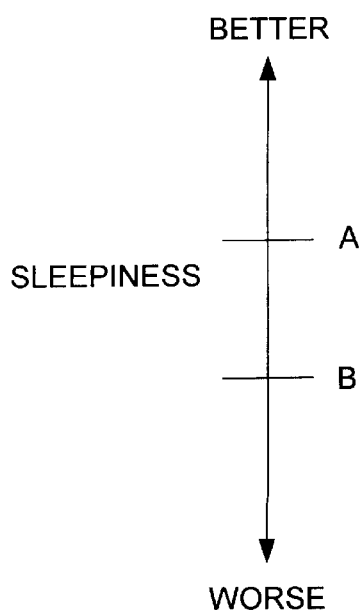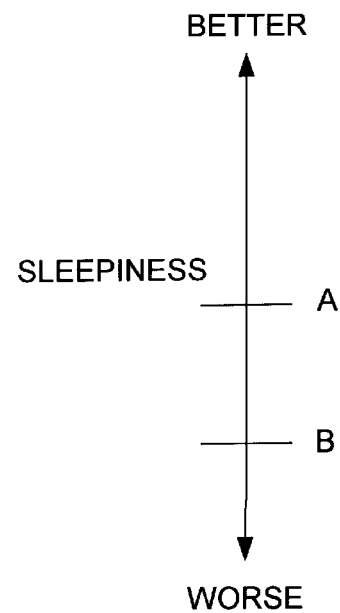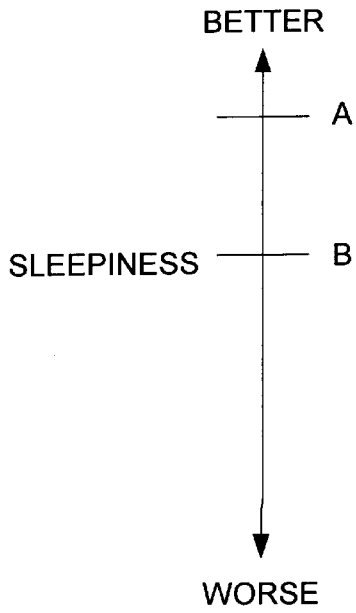
FIG. 2A  FIG. 2B  FIG. 4

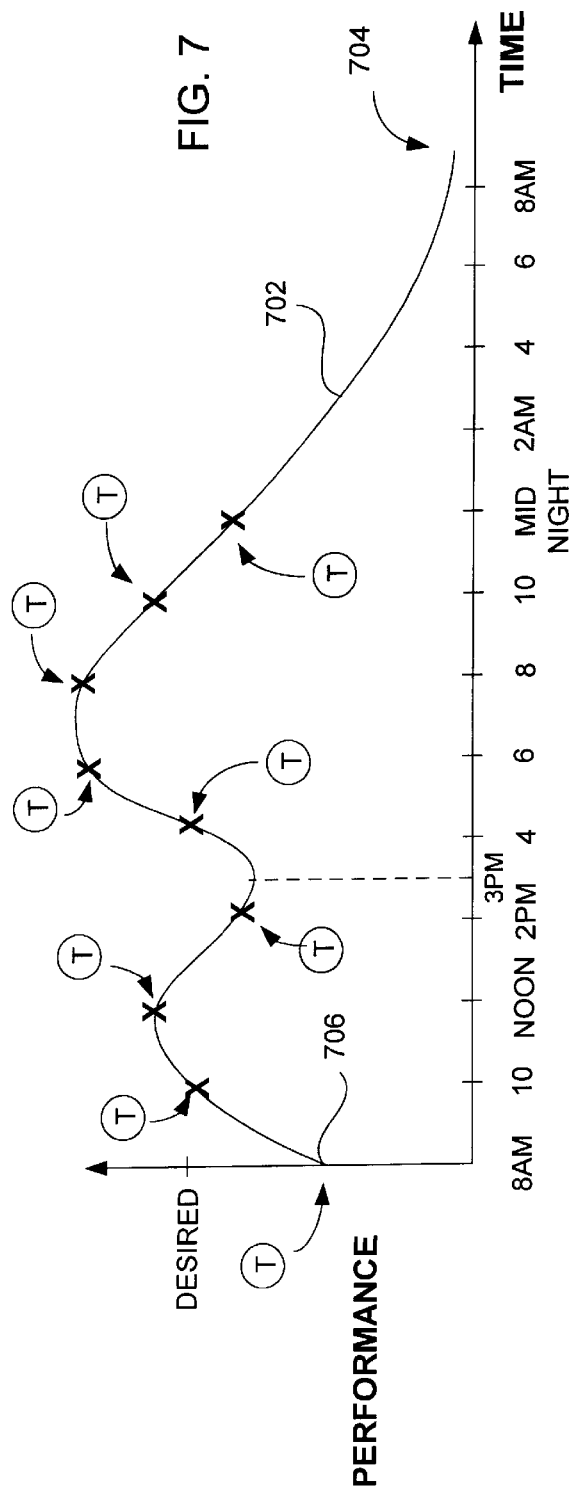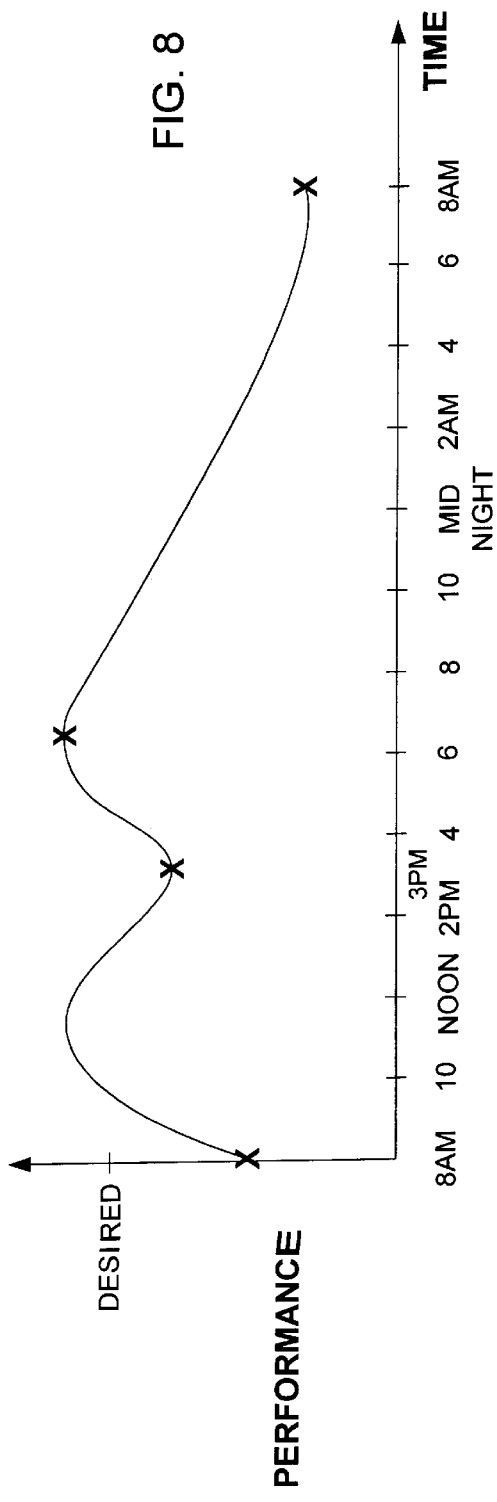

METHOD AND APPARATUS FOR DYNAMICALLY TAILORING BIOCHEMICAL BASED THERAPY PROGRAMS IN HUMAN

This application is a continuation of U.S. application Ser. No. 09/052,838 entitled "Methods and Apparatus for Improving Biochemical-based Therapy in Humans," Docket No. SLC714A/STLCP003, filed on Mar. 31, 1998, and incorporated by reference herein.

BACKGROUND OF THE INVENTION

The present invention relates to techniques for improving biochemical-based therapy in a human. More particularly, the present invention relates to computer-implemented techniques for employing task-controlled behavioral assessment and behavioral training, such as stimulus/response exercises or games, to improve the efficacy of the biochemical-based therapy to reduce or eliminate the need thereof, or to reduce the undesirable side effects of the biochemical-based therapy in a human.

The use of biochemical-based therapy involving various biological and/or chemical compounds to address a physiological and/or mental condition in humans is known. Generally speaking, biochemical-based therapy involves repeatedly administering a preset dosage of a biological/chemical compound to a human (by injection, ingestion, transdermal techniques, and/or the like) over a period of time to improve the aforementioned physiological and/or mental condition. By stimulating the human in a pharmacological manner, it is often hoped that over time the physiological and/or mental condition to be addressed would improve to the point where the biochemical-based therapy is no longer needed.

To facilitate discussion, scale 100 of FIG. 1 represents a scale of performance level relating to a particular physiological and/or mental condition (such as, for example, attention span) on which a desired condition 102 represents the level of performance acceptable and/or desirable in a human. On scale 100, the levels of performance by a human A and a human B are shown. As depicted, the levels of performance of humans A and B fall short of desired condition 102. To bring the levels of performance of humans A and B closer to desired condition 102, the prior art biochemical-based therapy may involve administering preset dosages of a biological and/or chemical compound over a predefined period of time to human A and human B. By driving the improvement in a pharmacological manner, it is commonly hoped that over time the level of performance of humans A and B in this particular condition (e.g., attention span) may improve to the point where the dosages of biological and/or chemical compound may be reduced or terminated altogether.

It has been found, however, that when the improvement in human is driven solely by pharmacological effects of the administered biological/chemical compounds, humans tend to develop a tolerance condition, which over time may actually require an increase in the required dosage of the biological/chemical compounds administered.

Furthermore, for many administered biological/chemical compounds, there are side effects which must be tolerated and/or addressed with even more biochemical-based therapy (e.g., by administering yet other biological/chemical compounds to address the side effects). With reference to FIG. 2A, scale 200 represents the scale of performance pertaining to a particular condition of the human, which condition may be impacted as an undesirable side effect of the biochemical-based therapy administered to address the first ailment or deficit (e.g., such as the attention deficit condition of the example of FIG. 1). Scale 200 may represent, for example, the level of sleepiness or hand shaking in the human subject.

In FIG. 2A, the intrinsic levels of sleepiness, i.e., the levels of sleepiness in the absence of the biochemical-based therapy, of humans A and B are shown. In FIG. 2B, the administration of the biochemical-based therapy to address the unrelated attention deficit condition has undesirably increased the levels of sleepiness in humans A and B. As mentioned earlier this undesirable side effect must, in the prior art, either be tolerated (such as avoiding driving) or addressed with yet more biochemical-based therapy (such as ingesting caffeine).

Furthermore, it is recognized that even if immediate side effects are not observed in connection with a given biochemical-based therapy regime, there are lingering concerns regarding the long term effects associated with the administration of biological/chemical compounds which may not be naturally produced by human. Accordingly, recent trends have shown an increased reluctance on the part of people to continue a biochemical-based therapy program for an extended period of time and/or to take increasing dosages of biological/chemical compounds (due to, e.g., the aforementioned tolerance problem) to address a particular physiological and/or mental condition.

In view of the foregoing, there are desired improved techniques for improving the efficacy of the biological/chemical compounds employed in biochemical-based therapy and/or for reducing the undesirable side effects thereof without employing additional biochemical-based therapy.

SUMMARY OF THE INVENTION

The invention relates, in one embodiment to a computer-implemented method for dynamically tailoring dosages of a biochemical compound administered to a human under a biochemical-based therapy program. The method includes administering a first plurality of stimulus exercises to the human over a period of time. The first plurality of stimulus exercises are administered to the human after at least one administration of the biochemical compound. The method also includes measuring responses from the first plurality of stimulus exercises to assess efficacy levels of the biochemical portion on the human as a function of time over the period of time. The method further includes dynamically modulating the dosages of the biochemical compound responsive to the efficacy levels measured from the first plurality of stimulus exercises. The modulating results in a first dosage configured to be administered to the human at a first administration time and a second dosage different from the first dosage configured to be administered to the human at a second administration time different from the first administration time.

In another embodiment, the invention relates to a computer-controlled apparatus for dynamically tailoring dosages of a biochemical compound administered to a human under a biochemical-based therapy program. The computer-controlled apparatus includes means for administering a first plurality of stimulus exercises to the human over a period of time. The first plurality of stimulus exercises are administered to the human after at least one administration of the biochemical compound. The computer-controlled apparatus also includes means for measuring responses from the first plurality of stimulus exercises to assess efficacy levels of the biochemical portion on the human as a function of time over the period of time. The computer-controlled apparatus further includes means for dynamically determining the dosages of the biochemical compound responsive to the efficacy levels measured from the first plurality of stimulus exercises. The dynamically determining results in tailored dosages responsive to the efficacy levels, including a first dosage configured to be administered to the human at a first administration time and a second dosage different from the first dosage configured to be administered to the human at a second administration time different from the first administration time.

In yet another embodiment, the invention relates to a computer-controlled apparatus for tailoring dosages of a biochemical compound administered to a human under a biochemical-based therapy program. The computer-controlled apparatus includes a first transducer and a computer configured to furnish first signals representative of a first plurality of stimulus exercises to the first transducer, thereby causing the transducer to deliver first stimuli representative of the first signals to the human over a period of time. The first stimuli are delivered after at least one administration of the biochemical compound to the human.

The computer-controlled apparatus also includes a second transducer coupled to the computer, the second transducer being configured to measure responses from the human and to furnish data representative of the responses as second signals to the computer. The responses represent reactions from the human responsive to the first stimuli after the at least one administration of the biochemical compound. The computer further is configured to ascertain from the responses efficacy levels of the biochemical compound as a function of time and to dynamically determine the dosages of the biochemical compound responsive to the efficacy levels ascertained from the responses. The computer further is configured to ascertain, responsive to the efficacy levels ascertained from the responses, the dosages which include a first dosage configured to be administered to the human at a first administration time and a second dosage different from the first dosage configured to be administered to the human at a second administration time different from the first administration time.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings in which like reference numbers refer to like items and in which:

FIG. 1 depicts, to facilitate discussion, a performance scale of a particular condition in human, including the acceptable level of performance and the levels of performance of humans A and B.

FIG. 2A depicts the intrinsic levels of performance of a condition by humans A and B.

FIG. 2B depicts the levels of performance by humans A and B with regard to the condition of FIG. 2A, showing how those levels of performance have been adversely impacted as unwanted side effects by the prior art biochemical-based therapy.

FIG. 3 depicts the intrinsic levels of performance of humans A and B on the scale of FIG. 1 after a behavioral training program is employed.

FIG. 4 depicts the intrinsic levels of performance of humans A and B on the scale of FIG. 2A after a behavioral training program is employed, showing that the unwanted side effect is reduced thereby.

FIG. 7 illustrates a curve showing the performance level of a human subject over time responsive to a biochemical-based therapy program.

FIG. 8 illustrates a curve showing the performance level over time of the human subject of FIG. 7 after a biochemical-based therapy program that has been tailored in accordance with one aspect of the present invention is administered.

DETAILED DESCRIPTION OF THE PREFERRED EMBODIMENTS

Figure 5:
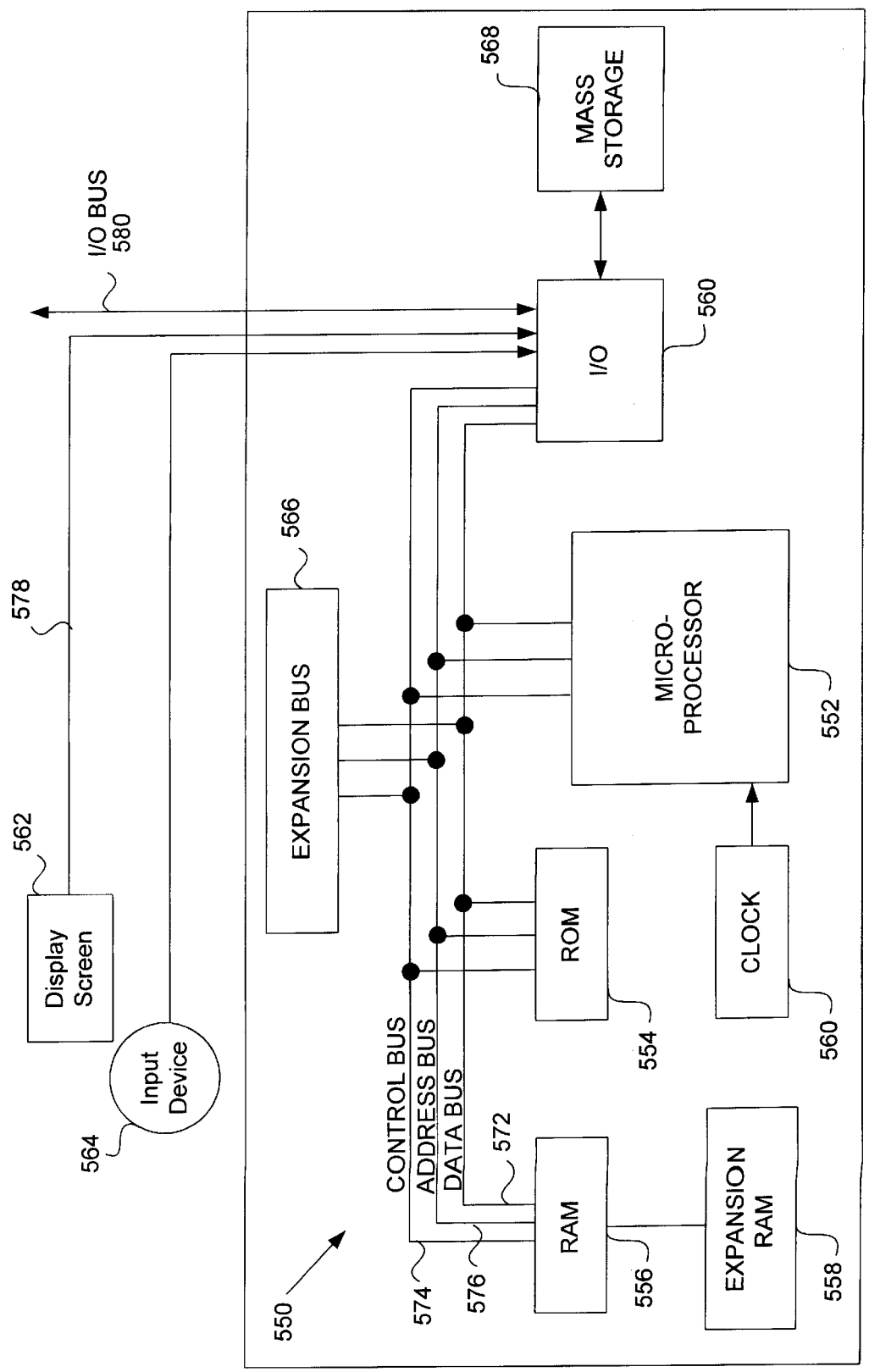
FIG. 5 illustrate, in accordance with one embodiment of the invention, the computer-controlled apparatus for administering behavioral training to human to improve the biochemical-based therapy.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In accordance with one aspect of the present invention, there is provided a computer-implemented technique for improving the efficacy of and/or for reducing the undesirable side effects of the biological/chemical compounds employed in a biochemical-based therapy program. In the preferred embodiment, the computer-implemented technique of the present invention involves employing stimulus/response exercises or games that are specifically selected to improve the intrinsic level of performance of a human in a particular condition of interest (e.g., attention span) so that the dosages of biological/chemical compounds required in the biochemical-based therapy regime become progressively smaller or eliminated all together over time. To put it differently, the computer-implemented technique of the present invention simulates the pharmacological effects of the administered biological/chemical compounds to drive the improvement in the level of performance without actually employing a biological/chemical compound.

While not wishing to be bound by theory, it is believed that when a human is trained in a particular behavioral training regime, the connections among relevant cells are strengthened such that the intrinsic level of performance (i.e., the level of performance that exists in the absence of the biological/chemical usage) related to the targeted condition increases. Over time, behavioral training may increase the intrinsic level of performance of the targeted condition to the point where it is possible to reduce or eliminate the need for the biological/chemical compound of the biochemical-based therapy.

In accordance with one hypothesis, cells may be thought of as being packed together closely in human. The cells compete for resources such as minerals or chemicals, which are needed for cell maintenance and growth. Synchronized activities between groups of cells invigorate connection strengths and stimulate access to resources by those cells. On the other hand, groups of cells that do not participate in synchronized activities are less competitive, have weaker inputs because they have less vigorous connections and thereby have less access to the resources. It is believed that behavioral training using stimulus/response exercises improves the coincident input-dependent activities (and synchronization) between groups of cells, thereby improving their functionality and vigor and their access for the highly competitive resources needed for cell growth and/or maintenance. In other words, the administration of stimulus/response exercises modifies the cells in a physical way, i.e., they form and strengthen connections between them in a way that cells that are not similarly simulated do not.

With a biochemical-based therapy regime based solely on the administration of preset dosages of biological/chemical compounds (as was done in the p/a), it is believed that the biological/chemical compounds simulate the synchronized connections between groups of cells, i.e., the human body temporarily responds as if the cells interact in a synchronized manner. But the cells themselves did not interact. Instead, they merely react, or cause the human body to react, to the pharmacological effects of the administered biological/chemical compounds. Because the cells are not actually stimulated in natural ways, the administration of the biological/chemical compounds can be regressive, causing the human body to require ever higher dosages of the biological/chemical compounds to make up for the deficiencies in activity and vigor. Over time, tolerance to the administered biological/chemical compounds occurs, sometimes to the point where the administered biological/chemical compounds are no longer effective irrespective of the dosage.

It is appreciated by the inventors herein that, contrary to conventional theories, the human brain is not hard-wired even in adult humans, and that the connections between cells are quite plastic and can be manipulated, modified, and/or strengthened through targeted behavioral training. It is further appreciated by the inventors herein that there is a cause-and-effect relationship, albeit a nonobvious one, between stimulus/response exercises and the efficacy of the administered biological/chemical compounds. From these insights, it is further appreciated that a behavioral training regime employing for example stimulus/response exercises, may be administered to a human to specifically target and strengthen the synchronized activities between groups of cells to stimulate the improvement of a physiological and/or mental condition in the human so as to reduce and/or eliminate over time the required dosages of biological/chemical compounds of the prior art biochemical-based therapy. Since a behavioral training programs can be targeted with much greater precision than a biochemical-based therapy program, the use of behavioral training to improve the biochemical-based therapy advantageously reduces the possibility of undesirable and/or unpredictable side effects before, during, and/or after the implementation of the training program.

The features and advantages of these aspects of the invention, as well as other aspects of the present invention, may be better understood with reference to the figures and discussions that follow. FIG. 3 depicts scale 100 of FIG. 1, along with desired condition 102. In the illustration of FIG. 3, the intrinsic levels of performance of humans A and B are shown to have moved closer toward desired condition 102 via targeted stimulus/response exercises, which have been administered over time to humans A and B. Because of the improvement driven by the targeted behavioral modification training, the dosages of biological/chemical compounds required by the human may be reduced or eliminated altogether. By way of example, the intrinsic level of performance of human A in the targeted condition (e.g., attention span) may have improved via behavioral training to the point where it is no longer necessary to administer the biological/chemical compound of the biochemical-based therapy program to human A. The intrinsic level of performance of human B may also have increased through behavioral training such that the required dosage is substantially reduced. In effect, behavior training may be employed to improve the efficacy of the administered biological/chemical compounds on the human. Because a behavioral training program can be targeted at the condition to be remedied and typically does not affect other conditions/areas in the way that biological/chemical compounds do in humans, such improvement advantageously does not come at the expense of undesirable and/or unwanted side effects.

As mentioned, behavioral training via stimulus/response exercises may also be employed to reduce undesirable side effects of the biochemical-based therapy and/or of other types of therapy such as surgery, radiation, or the like. To simplify the discussion herein, only the side effects of biochemical-based therapy will be discussed in greater detail. It should be understood, however, that the techniques disclosed herein also apply to reduce undesirable side effects from other types of therapy as well (e.g., other environmental or procedures such as surgery or radiation).

FIG. 4 illustrates scale 200 of FIGS. 2A and 2B, which represents a condition undesirably affected by the administration of the biological/chemical compound to address the primary condition of FIG. 1. In FIG. 4, targeted behavioral modification training (via stimulus/response exercises) have decreased the undesirable side effects such that the intrinsic level of side effects (i.e., the level of side effect that exists in the absence of any biochemical-based therapy to address the side effects) is reduced. As in the case of FIG. 3, the reduction of the undesirable side effects may be sufficient to either reduce any need to address them via another biochemical-based therapy program or to eliminate such need altogether.

The reduction in the intrinsic level of undesirable side effect is possible since the behavioral modification training can be specifically targeted such that improvement in one condition may be achieved without adversely impacting other conditions in the human. This is unlike the prior art approach wherein the consumption of biological/chemical compounds may affect different groups of cells in sometimes undesirable and unpredictable manners. As such, it is possible to reduce the undesirable side effects without causing yet other side effects and/or reducing the effectiveness of the biochemical-based therapy program (or the behavioral training program) administered to the address the original condition (e.g., the attention deficit condition).

As mentioned, the behavioral training program is preferably administered using a computer-implemented technique. FIG. 5 illustrates, in accordance with one embodiment of the invention, an exemplary computer-controlled apparatus, including computer 550, for delivering computer-controlled stimuli to the human subject to improve the biochemical-based therapy. Depending on the behavioral training regime chosen, the stimulus may be delivered through any of the senses or a combination thereof. Responses from the human subject may be received by the computer and evaluated in any number of ways, some of which are discussed further below.

Referring to FIG. 5, a computer system 550 in accordance with one embodiment of the present invention includes a central processing unit (CPU) 552, read only memory (ROM) 554, random access memory (RAM) 556, expansion RAM 558, input/output (I/O) circuitry 560, display assembly 562, input device 564, and expansion bus 566. Computer system 550 may also optionally include a mass storage unit 568 such as a disk drive unit or nonvolatile memory such as flash memory and a real-time clock 560. In one embodiment, mass storage unit 568 may include units which utilizes removable computer readable media, such as floppy disks, opto-magnetic media, optical media, and the like for the storage of programs and data.

CPU 552 is preferably a commercially available, single chip microprocessor such as one of the Intel X86 (including Pentium™) or Motorola 680XX family of chips, a reduced instruction set computer (RISC) chip such as the PowerPC™ microprocessor available from Motorola, Inc, or any other suitable processor. CPU 552 is coupled to ROM 554 by a data bus 572, control bus 574, and address bus 576. ROM 554 may partially contain the basic operating system for the computer system 550. CPU 552 is also connected to RAM 556 by busses 572, 574, and 576 to permit the use of RAM 556 as scratch pad memory. Expansion RAM 558 is optionally coupled to RAM 556 for use by CPU 552. CPU 552 is also coupled to the I/O circuitry 560 by data bus 572, control bus 574, and address bus 576 to permit data transfers with peripheral devices.

I/O circuitry 560 typically includes a number of latches, registers and direct memory access (DMA) controllers. The purpose of I/O circuitry 560 is to provide an interface between CPU 552 and such peripheral devices as display assembly 562, input device 564, mass storage 568, and/or any other I/O devices. I/O circuitry 560 may also include analog-to-digital (A/D) converters, digital-to-analog (D/A) converters, as well as other control circuits for controlling and receiving feedback data from the I/O devices. The I/O devices suitable for generating stimuli to be administered to the human subject and for receiving responses therefrom may be coupled to I/O bus 580 of computer 550. Display assembly 562 of computer system 550 is an output device for displaying objects and other visual representations of data, as well as for generating visual stimuli in one embodiment.

The screen for display assembly 562 can be a device that uses a cathode-ray tube (CRT), liquid crystal display (LCD), or the like, of the types commercially available from a variety of manufacturers. Input device 564 can be a keyboard, a mouse, a stylus working in cooperation with a position-sensing display, or the like. Alternatively, input device 564 can be an embedded RF digitizer activated by an "active" RF stylus. As a further alternative, input device 564 may be any type of switch capable of communicating a test subject's response to computer system 550. Therefore, as used herein, the term input device will refer to any mechanism or device for entering data and/or pointing to a particular location on a screen of a computer display. One or more input devices may be provided to control computer 550 and/or to receive responses from the test subject. Note that the responses to be received and employed in the behavioral training program may include not only behavioral responses (e.g., behaviors exhibited by the human subject such as clicking on a mouse) but also physiological responses (e.g., EKG, EEG, MEG, or any other measurable physiological responses). The aforementioned input devices, appropriately chosen for the response to be obtained, are available from a variety of vendors and are well known in the art.

Some type of mass storage 568 is generally considered desirable. However, mass storage 568 can be eliminated by providing a sufficient amount of RAM 556 and expansion RAM 558 to store user application programs and data. It is generally desirable to have some type of long term mass storage 568 such as a commercially available hard disk drive, nonvolatile memory such as flash memory, battery backed RAM, PC-data cards, or the like.

The stimuli generators may include headphones (for delivering auditory stimuli), computer-controlled probes (for delivering touch stimuli), visual stimuli generators (for delivering visual stimuli), physiological stimulatory generation or probes (which may be internally or externally placed) and/or virtual reality apparatus (for delivering stimuli to and receiving responses from the human subject in a virtual manner through any of the senses). In general, these stimuli generators may interface with computer system 550 via an appropriate interface circuit, which may be either internal or external to computer 550 and/or dedicated to the I/O device. A visual stimuli generator may be implemented by, for example, any light generating device such as a light bulb, a flash device, another computer display screen or the like if such is employed instead of display screen 562 of computer 550 for providing visual stimuli to the test subject. The virtual reality apparatus may be implemented by, for example data gloves, virtual goggles, data-enabled body suits, or the like, each of which may be able to both deliver the stimuli to the test subject as well as sense the responses therefrom. An optional input device, such as a switch, may also be provided for receiving responses from the test subject. The optional input device may be provided when it is desired to receive responses to the test stimuli from the test subject through an input device other than input device 564 of computer 550.

In operation, computer system 550 is employed to generate control signals to the stimuli generator(s) to produce the stimuli of the various training or condition assessment regimes. Different behavioral-based assessment/training regimes may employ stimuli having different intensity, duration, and spatial parameters, and these parameters may be varied as desired even in the same training regime or even during a given training session. These stimuli are then furnished to the test subject for assessment and/or training, and the responses from the test subject may then be recorded by an input device and analyzed by CPU 552 (for accuracy, delay, or other parameters indicative of the subject's level of performance). If desired, feedback to the test subject may be given at various stages of the test(s) via, for example, display assembly 562.

It should be borne in mind that although computer system 550 is discussed in some detail herein to facilitate discussion, the invention may be practiced using a variety of suitable computer-implemented technique. In general, any suitable computer system may be employed for generating control signals to the stimuli generators and receive feedback from the input device(s). Further, the inventive training technique disclosed herein may be implemented via a computer network, such as a local area network (LAN), wide area network (WAN) or a global computer network such as the Internet. In the latter cases, the inventive computer-implemented behavioral training technique may be implemented at least in part as downloadable computer software and data (e.g., applets such as JAVA™ applets from Sun Microsystems Inc. or ActiveX from Microsoft Corp. of Redmond, Wash.). The downloadable computer software and data may be kept on one or more servers on the network, accessible by any client computer or terminal capable and authorized for such access. The client computer/terminal may then be employed to control an appropriate stimuli generator and to gather responses from the test subject. To facilitate assessment and/or training, the downloadable computer software and data can be downloaded once and reused over and over at the client computer/terminal. Alternatively, the downloadable computer software and data can be downloaded for each individual session via the network as needed. In some cases, the computer software may be executed at the servers themselves, with program outputs transmitted to the client computer/terminal for interfacing with the I/O devices. Network computing techniques and implementations therefor are well known in the art and are not discussed in great detail here for brevity's sake.

Figure 6:
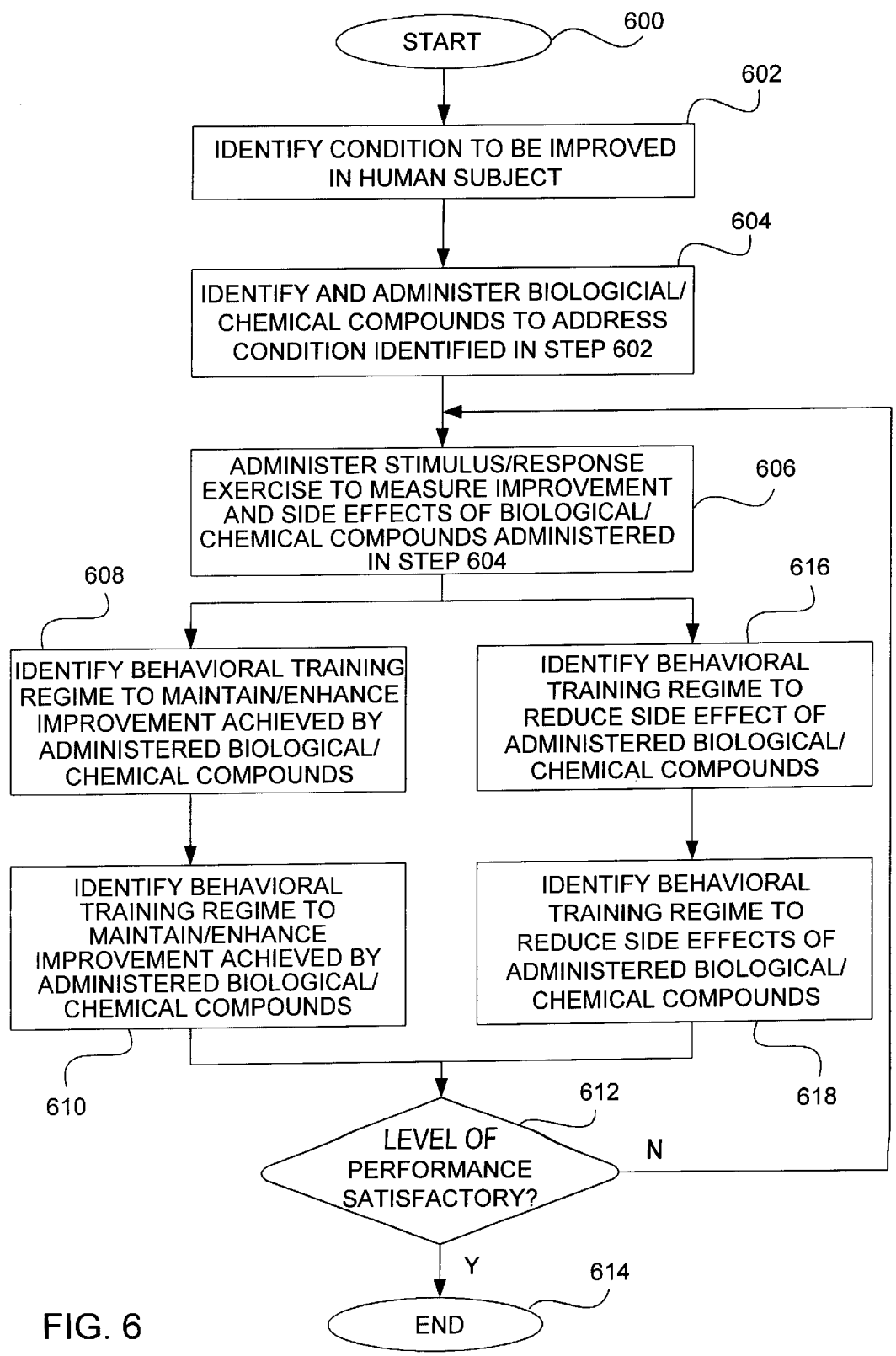
FIG. 6 illustrates, in accordance with one embodiment of the invention, the steps of the computer-implemented behavioral training that is capable of improving the efficacy of the biochemical-based therapy and/or reducing the side effects thereof.

FIG. 6 illustrates, in accordance with one embodiment of the present invention, the major steps of the computer-implemented method for improving the biochemical-based therapy in a human. Note that since these steps may be performed over time, each step may be accomplished, in the same or different iterations of the computer-implemented technique, in the same computer/terminal or in a similarly enabled computer/terminal. Accordingly the term "computer" as employed herein should be construed to cover any computer or terminal that is capable of performing the disclosed step under discussion and does not necessarily limit the application of the entire sequence of steps to any single computer or terminal (i.e., the different steps may be performed on different computers or on a single computer as convenient and/or appropriate.

In step 602, a stimulus/response exercise or a battery of stimulus/response exercises is administered to the human to identify the condition or conditions to improve. Step 602 is optional since there exists other diagnostic techniques in the art to identify a particular ailment or deficiency in a human without employing the stimulus/response exercises. Such diagnostic techniques may include, for example, blood testing, radiology-based techniques, identification through symptoms exhibited by the human subject, or the like.

In step 604, a biological/chemical compound useful in addressing the condition identified in step 602 is administered in doses to the human as part of a biochemical-based therapy program. The selection of a particular biological/chemical compound useful for addressing a particular condition is conventional in the art and may be performed by consulting widely available reference works, including literature from the pharmaceutical companies.

In step 606, a stimulus/response exercise or a battery of stimulus/response exercises is administered, preferably using a computer-implemented technique, to the human to measure the improvement and side effects, if any, of the administered biological/chemical compounds. If an improvement is detected in step 606, the method proceeds to step 608 wherein the particular stimulus/response exercise(s) useful in enhancing/maintaining the improvement achieved by the administered biological/chemical compound is identified. It should be appreciated that the specific stimulus/response exercise(s) identified in step 606 varies depending on the condition to be remedied and may be derived theoretically or empirically in a laboratory setting. If attention deficit is to be remedied, for example, the exercise may involve stimulus/response games designed to hold the human's attention for ever increasing periods of time.

In step 610, the identified stimulus/response exercises of step 608 are then administered to the human, preferably as battery of exercises over time to maintain and/or enhance the improvement achieved by the biological/chemical compound administered in step 606.

In step 612, the level of performance pertaining to the condition identified in step 602 may be measured again using a conventional testing and/or assessment technique or using an appropriate stimulus/response exercise as an assessment tool. If the level of performance is satisfactory (e.g., if the result of a stimulus/response game indicates that the human has satisfactorily improved in his ability to focus and/or pay attention over time), the method proceeds to step 614 wherein it is understood that the improvement is such that additional dosages of the biological/chemical compounds are no longer necessary.

On the other hand, if the level of performance measured in step 612 is still unsatisfactory, i.e., the intrinsic level of performance is not satisfactory in view of the desired level of performance in the particular condition in question, the method returns to step 606 wherein additional stimulus/response exercises may be administered, either alone or in conjunction with a dosage of the biological/chemical compound that is sufficient to bring the level of performance up to a predefined level of performance in this iteration.

Note that in subsequent iterations, it may be unnecessary to identify again the stimulus/response exercise(s) that is useful in maintaining and/or enhancing the improved performance since the stimulus/response exercise identified in a previous iteration on this human may be employed without requiring identifying step 608 to be undertaken for every iteration. On the other hand, it may be desirable to identify a different stimulus/response exercise in a subsequent iteration to maximize the chance of improving the biochemical-based therapy program. Thus, the same stimulus/response exercise may be employed in different iterations or different stimulus/response exercises may be employed instead.

The stimulus/response exercise may be administered again in step 610 to further improve the intrinsic level of performance. Thereafter, the method continues until the intrinsic level of performance rises to the level where the biological/chemical compound is no longer needed or where it is felt that another or different biological/chemical compound may be required.

If the administered biological/chemical compound produces an undesirable side effect (as detected in step 606), the method may proceed from 606 to step 616 wherein a stimulus/response exercise useful for reducing the undesirable side effects of the administered biological/chemical compound is identified. As in step 616, the specific stimulus/response exercise useful in reducing a particular identified side effect may vary depending on the side effect to be remedied and may be ascertained theoretically or empirically in a laboratory setting.

In step 618, the stimulus/response exercise(s) identified in step 616 that is useful for reducing the undesirable side effect of the biochemical-based therapy administered to address the original condition (e.g., attention deficit) is administered to the human. Thereafter, the level of performance of the human pertaining to this particular side effect condition (e.g., the aforementioned sleepiness, or hand shaking) is ascertained in step 606 to determine whether further training is necessary.

As can be appreciated from the foregoing, the invention advantageously improves the efficacy of the administered biological/chemical compound of the prior art biochemical-based therapy in a manner that is specifically targeted to the condition to be improved and that does not require the consumption of other biological/chemical compounds. Since the behavioral training is specifically targeted, the possibility of unwanted side effects from the behavioral training is substantially reduced. Over time, behavioral training advantageously improves the intrinsic level of performance of the human subject such that, as mentioned, the biological/chemical consumption is reduced or eliminated altogether.

The use of behavioral training to reduce the unwanted side effects of the administered biological/chemical compounds also offers similar advantages. The targeted nature of behavioral training minimizes the possibility of introducing yet other unwanted side effects when trying to reduce the first unwanted side effect. Since the reduction in unwanted side effects is accomplished without employing still more biological/chemical compounds, the invention advantageously offers another way for humans who do not wish to treat the unwanted side effect with additional biological/ chemical compounds to minimize the suffering associated with unwanted side effects.

It should be noted that although the behavioral training is described as being performed after at least one administration of the biochemical-based therapy regime, it is also possible to employ behavioral training to reduce/eliminate the dosage prior to the administration of the biochemical-based therapy. Furthermore, although the behavioral training is described herein with reference to improving the negative consequences of administered biological/chemical compounds, the invention also applies to reducing and/or eliminating the negative consequences associated with any other biochemical or environmental therapies or procedures (such as surgery, radiation, or the like).

In accordance with one aspect of the present invention there is provided a computer-implemented method for dynamically evaluating over time the benefit of a particular biological/chemical compound of a biochemical-based therapy program in order to tailor the dosages of that biological/chemical compound to the time of the highest need and/or benefit. In contrast to prior art techniques of administering the biochemical-based therapy wherein a given dosage of biological/chemical compound is typically administered periodically or on some predetermined time schedule, the invention involves dynamically evaluating, using stimulus/response assessment exercises at a fairly high frequency, the need/benefit of the administered biological/ chemical compound as a function of time. With the information provided by the high frequency stimulus/response exercises, the dosages of the biological/chemical compound administered over time may be tailored to enhance/maintain the benefit and/or to reduce the undesirable side effect(s) thereof.

It is recognized by the inventors herein that the efficacy of a particular biological/chemical compound in a human subject may vary from one subject to the next. Even in the same human subject, the efficacy may not be a linear function of time and may vary over time due to hormonal, biological, and/or other factors. To illustrate, FIG. 7 depicts a graph of the effectiveness of an exemplary biological/chemical compound in a given biochemical-based therapy program versus time. In FIG. 7, the time scale is shown to be the time of day although this time scale is arbitrary and may span any relevant time period (e.g., minutes, days, weeks, months and the like). In FIG. 7, curve 702 depicts the level of therapeutic efficacy of a biological/chemical compound in an exemplary human subject, which biological/chemical compound is administered at 8:00 a.m. and again at 3:00 p.m. in the example of FIG. 7. As can be seen in FIG. 7, the therapeutic effect rises in the human after the biological/chemical compound is administered and, as would be expected, decays slowly over time thereafter.

The effect of tolerance is also shown in FIG. 7 as the efficacy the administered biological/chemical compound at point 704 in the human appears lower than the efficacy level achieved when the biological/chemical compound was administered 24 hours earlier, i.e. at point 706 in FIG. 7. Tolerance occurs because of the tendency of cells to become increasingly dependent on the pharmacological effects provided by the administered biological/chemical compound. Over time, the human subject of FIG. 7 may need a higher dosage of the administered biological/chemical compound in order to obtain the same level of benefit.

In accordance with one aspect of the present invention, a plurality of stimulus/response exercises are administered at some predefined frequency (which may be fixed or variable) throughout the relevant time period (e.g., the day in the case of the example of FIG. 7) in order to dynamically ascertain the efficacy of the administered biological/chemical compound. From the behavioral assessment data acquired from the stimulus/response exercises, the dosages may be tailored to achieve the desired level of performance without over-administering or under-administering the dosages at any given time.

As shown in FIG. 7, behavioral/physiological assessment via the administration of the stimulus/response exercises (shown by the letter "T" to be performed every two hours between 8 a.m. and midnight in the example of FIG. 7) may reveal that a relatively large dose may be required at 8:00 a.m., and a relatively smaller dose may be sufficient at 3 p.m. in order to achieve/maintain the desired level of therapeutic efficacy. Accordingly, the dosage given at 3 p.m. in the example of FIG. 8 may be reduced (relative to the dosage given at 3 PM in the example of FIG. 7) to lower the likelihood of over-dosage and/or reduce the undesirable side effect(s) and to delay and/or eliminate the tolerance effect while still achieving the desired level of performance. By tailoring the dosages to either reduce and/or eliminate the tolerance effect, the reduction of dosages over time may be accelerated without adversely affecting efficacy.

The behavioral/physiological assessment may also be employed to identify the possibility of employing behavioral modification exercises to reduce the dosage of the administered biological/chemical compound required at a particular time. By way of example, behavioral/physiological assessment through the administered stimulus/response exercises may suggest that some behavioral training at 2 p.m. may improve the human subject's intrinsic level of performance sufficiently to permit the dosage required at 3:00 p.m. to be reduced or eliminated. In this manner, the dynamic assessment and dosage tailoring technique of the present invention may be employed in conjunction with the computer implemented technique for improving the biochemical-based therapy disclosed earlier in connection with FIGS. 3–6 in order to reduce and/or eliminate the biological/chemical doses (and/or reduce/eliminate the undesirable side effects) over time.

Figure 9:
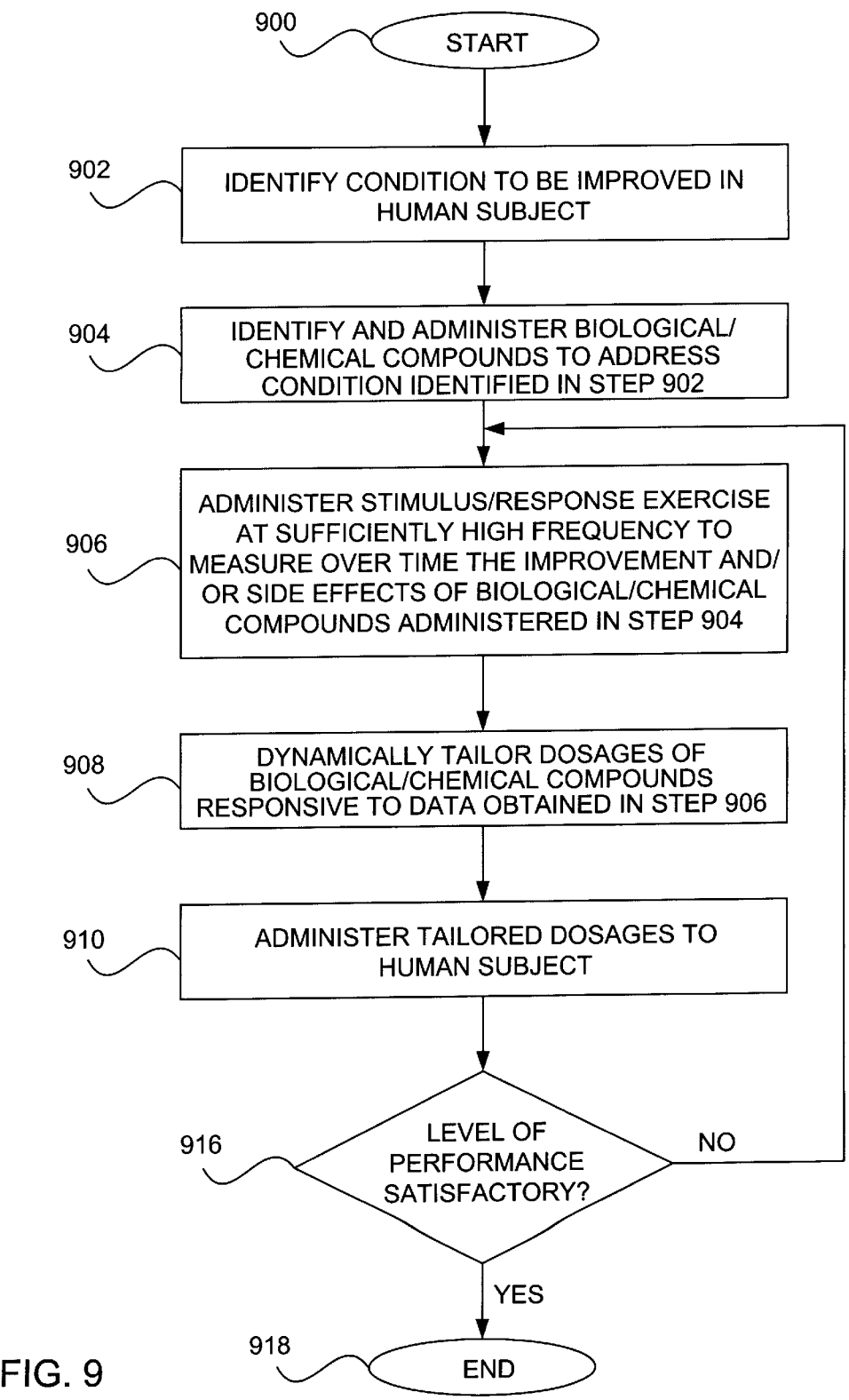
FIG. 9 illustrates, in accordance with one embodiment of the invention, the steps of the computer-implemented method for dynamically tailoring a biochemical-based therapy program.

FIG. 9 illustrates, in accordance with one embodiment of the present invention, the major steps of the computer-implemented method for dynamically tailoring dosages over time in order to reduce the required dosages and/or to reduce undesirable side effect(s) in a given human subject. Again, note that since these steps may be performed over time, each step may be accomplished, in the same or different iterations of the computer-implemented technique, in the same computer/terminal or in a similarly enabled computer/terminal.

In step 902, a stimulus/response exercise or a battery of stimulus/response exercises is administered to the human subject to identify the condition or conditions to improve. Step 902 is optional since, as mentioned earlier in connection with step 602, there exist other diagnostic techniques in the art to identify a particular ailment or deficiency in a human without employing the stimulus/response exercises. Such diagnostic techniques may include, for example, blood testing, radiology-based techniques, identification through symptoms exhibited by the human subject, or the like.

In step 904, a biological/chemical compound useful in addressing the condition identified in step 902 is administered in doses to the human as part of a biochemical-based therapy program. The selection of a particular biological/chemical compound useful for addressing a particular condition is conventional in the art and may be performed by consulting widely available reference works, including literature from the pharmaceutical companies.

In step 906, a battery of stimulus/response exercises is administered, preferably using a computer-implemented technique, to the human to measure the improvement and side effects, if any, of the administered biological/chemical compounds over time. The frequency of the assessment exercises is preferably chosen such that the efficacy of the administered biological/chemical compound can be resolved with sufficient detail for tailoring the dosages. In general, if the assessment exercises are given at a higher frequency (e.g., every half hour), the efficacy of the administered biological/chemical compounds may be ascertained with a higher resolution than if the assessment exercises are given at a lower frequency (e.g., only every 8 hours). Obviously, the frequency needs to be appropriate in view of practical considerations such as the ability of the human subject to endure repeated behavioral/physiological assessment testing. By way of example, assessment exercises given every hour or every few hours (e.g., between about 2–12 hours) tend to work well for some conditions. For some other conditions, assessment exercises administered at an even lower frequency, e.g., every day, every few days, every week, or every month may also be appropriate.

The data pertaining to the efficacy of the administered biological/chemical compound as a function of time may then be employed in steps 908 and 910 to tailor the dosages in order to allow the human subject to achieve/maintain the desired level of performance to reduce the possibility of over-dosage, under-dosage, or tolerance. With reference to FIG. 8, for example, the data pertaining to the efficacy of the administered biological/chemical compound as a function of time may be employed to tailor the dosages such that the dosage given at 8:00 a.m. would be higher relative to the dosage required at 3 p.m. Of course, the data may be employed to either increase the dosage at a given administration time (if the data reveals that the original dosage is inadequate for that administration time) or to decrease the dosage at a given administration time (if the data reveals that the original dosage would be excessive for that administration time).

After some time period, it may be desirable to ascertain whether the tailored dosage program is effective or whether a new/different biological/chemical compound and/or a different dosage program is required. This assessment takes place in step 916. If the level of performance is satisfactory (either with or without the enhancement provided by the behavioral training), the method then proceeds to step 918 to end the administration of the biological/chemical compound. Otherwise, the method returns to step 906 to redesign another dosage program and/or to employ a new biological/chemical compound to address the condition identified.

Of course the data pertaining to the efficacy of the administered biological/chemical compound (acquired in step 906) may also be employed to tailor training to enhance/maintain the improvement due to the administered biological/chemical compound(s) or to reduce/eliminate the side effect(s) due to the administered biological/chemical compound(s) in the manner discussed earlier in connection with FIG. 6. In this case, the behavioral training may be administered in between administrations of the biological/chemical compounds to further reduce the dosage required at the next administration time (and the concomitant undesirable side effect, if any) or may be administered periodically to enhance/maintain the improvement achieved by the tailored dosages the biological/chemical compound(s) and/or to reduce the undesirable side effects thereof. One embodiment of the computer-implemented technique for doing so has been discussed in detail in connection with FIG. 6 and will not be repeated here for brevity's sake.

It should be mentioned that even though some attempts were made in the prior art to account for the needs of different human subjects, such attempts have been rather crude (e.g., changing dosages depending on whether the human subject is "adult" or "children" or whether the condition is "severe" or "mild"). This is because despite modern advances, not all is understood regarding how effective a specific biological/chemical compound may be in a specific human subject, and particularly how that effectiveness varies as a function of time in a specific human subject. Thus the invention differs significantly from prior art techniques of biochemical therapies, which typically do not tailor dosages to the response of a particular human subject to the administered biological/chemical compound, and which typically do not to modulate dosages as a function of time taking into account the behavioral/physiological assessment data that reveal a specific human subject's response to the administered biological/chemical compound.

With the use of the computer-implemented dynamic assessment and dosage tailoring technique disclosed herein, it is now possible for health care professionals to obtain high resolution data pertaining to the efficacy of a biological/chemical compound as a function of time in a specific human subject and to dynamically tailor the dosages to achieve/maintain a desired level of performance for the specific human subject even if the theoretical understanding underlying the efficacy may be incomplete. By dynamically employing the relatively high frequency behavioral/physiological assessment, the invention advantageously permits the dosages to be dynamically modulated as needed as a function of time and tailored for a given human subject to reduce the possibility of under-dosage, over-dosage, and/or tolerance.

While this invention has been described in terms of several preferred embodiments, there are alterations, permutations, and equivalents which fall within the scope of this invention. It is therefore intended that the following appended claims be interpreted as including all such alterations, permutations, and equivalents as fall within the true spirit and scope of the present invention.

What is claimed is:

1. A computer-implemented method for dynamically tailoring dosages of a biochemical compound administered to a human under a biochemical-based therapy program, comprising:

administering a first plurality of stimulus exercises to said human over a period of time, said first plurality of stimulus exercises being administered to said human after at least one administration of said biochemical compound;

measuring responses from said first plurality of stimulus exercises to assess efficacy levels of said biochemical portion on said human as a function of time over said period of time; and dynamically modulating said dosages of said biochemical compound responsive to said efficacy levels measured from said first plurality of stimulus exercises, said modulating results in a first dosage configured to be administered to said human at a first administration time and a second dosage different from said first dosage configured to be administered to said human at a second administration time, said second administration time being different from said first administration time.

2. The computer-implemented method of claim 1 further comprising:

identifying, responsive to said efficacy levels measured from said first plurality of stimulus exercises, a third administration time different from said first and second administration time, said third administration time representing a time prior to said second administration time at which a given stimulus/response exercise may be administered to improve an efficacy of said biochemical compound in order to reduce said second dosage at said second administration time; and administering, using said computer, said given stimulus/response exercise to said human at said third administration time to reduce said second dosage at said second administration time.

3. The computer-implemented method of claim 1 further comprising:

identifying, responsive to said efficacy levels measured from said first plurality of stimulus exercises, a third administration time different from said first and second administration time, said third administration time representing a time during said period of time at which a given stimulus/response exercise may be administered to reduce an undesirable side effect of said biochemical compound; and administering, using said computer, said given stimulus/response exercise at said third administration time to said human.

4. The computer-implemented method of claim 1 wherein said responses represent behavioral responses.

5. The computer-implemented method claim 4 wherein said responses represent physiological responses.

6. A computer-controlled apparatus for dynamically tailoring dosages of a biochemical compound administered to a human under a biochemical-based therapy program, comprising:

means for administering a first plurality of stimulus exercises to said human over a period of time, said first plurality of stimulus exercises being administered to said human after at least one administration of said biochemical compound;

means for measuring responses from said first plurality of stimulus exercises to assess efficacy levels of said biochemical portion on said human as a function of time over said period of time; and means for dynamically determining said dosages of said biochemical compound responsive to said efficacy levels measured from said first plurality of stimulus exercises, said dynamically determining results in tailored dosages responsive to said efficacy levels, including a first dosage configured to be administered to said human at a first administration time and a second dosage different from said first dosage configured to be administered to said human at a second administration time different from said first administration time.

7. The computer-controlled apparatus of claim 6 further comprising:

means for identifying, responsive to said efficacy levels measured from said first plurality of stimulus exercises, a third administration time different from said first and second administration time, said third administration time representing a time prior to said second administration time at which a given stimulus/response exercise may be administered to improve an efficacy of said biochemical compound in order to reduce said second dosage at said second administration time; and means for administering, using said computer, said given stimulus/response exercise to said human at said third administration time to reduce said second dosage at said second administration time.

8. The computer-controlled apparatus of claim 7 wherein said means for administering said given stimulus/response exercise is the same as said means for administering said first plurality of stimulus exercises.

9. The computer-controlled apparatus of claim 6 further comprising:

means for identifying, responsive to said efficacy levels measured from said first plurality of stimulus exercises, a third administration time different from said first and second administration time, said third administration time representing a time during said period of time at which a given stimulus/response exercise may be administered to reduce an undesirable side effect of said biochemical compound; and means for administering, using said computer, said given stimulus/response exercise at said third administration time to said human.

10. The computer-controlled apparatus of claim 9 wherein said means for administering said given stimulus/response exercise is the same as said means for administering said first plurality of stimulus exercises.

11. The computer-controlled apparatus of claim 6 wherein said responses represent behavioral responses.

12. The computer-controlled apparatus of claim 11 wherein said responses represent physiological responses.

13. A computer-controlled apparatus for tailoring dosages of a biochemical compound administered to a human under a biochemical-based therapy program, comprising:

a first transducer;

a computer configured to furnish first signals representative of a first plurality of stimulus exercises to said first transducer, thereby causing said transducer to deliver first stimuli representative of said first signals to said human over a period of time, said first stimuli being delivered after at least one administration of said biochemical compound to said human;

a second transducer coupled to said computer, said second transducer being configured to measure responses from said human and to furnish data representative of said responses as second signals to said computer, said responses representing reactions from said human responsive to said first stimuli after said at least one administration of said biochemical compound, said computer further being configured to ascertain from said responses efficacy levels of said biochemical compound as a function of time and to dynamically determine said dosages of said biochemical compound responsive to said efficacy levels ascertained from said responses, said computer further being configured to ascertain, responsive to said efficacy levels ascertained from said responses, said dosages which include a first dosage configured to be administered to said human at a first administration time and a second dosage different from said first dosage configured to be administered to said human at a second administration time different from said first administration time.

14. The computer-controlled apparatus of claim 13 wherein said computer is further configured to determine, responsive to said efficacy levels measured from said first plurality of stimulus exercises, a third administration time different from said first and second administration time, said third administration time representing a time prior to said second administration time at which a given computer-implemented stimulus/response exercise may be administered to improve an efficacy of said biochemical compound in order to reduce said second dosage at said second administration time, said computer-implemented apparatus further comprising a third transducer for administering said given computer-implemented stimulus/response exercise to said human at said third administration time to reduce said second dosage at said second administration time.

15. The computer-controlled apparatus of claim 14 wherein first transducer and said third transducer are the same.

16. The computer-controlled apparatus of claim 13 wherein said computer is further configured to determine, responsive to said efficacy levels measured from said first plurality of stimulus exercises, a third administration time different from said first and second administration time, said third administration time representing a time prior to said second administration time at which a given computer-implemented stimulus/response exercise may be administered to reduce an undesirable side effect of said biochemical compound, said computer-implemented apparatus further comprising a third transducer for administering said given computer-implemented stimulus/response exercise to said human at said third administration time.

17. The computer-controlled apparatus of claim 16 wherein first transducer and said third transducer are the same.

18. The computer-controlled apparatus of claim 13 wherein said responses represent behavioral responses.

19. The computer-controlled apparatus of claim 13 wherein said responses represent physiological responses.

* * * * *